United States Patent [19]

Goss

[11] Patent Number: 4,622,920

[45] Date of Patent: Nov. 18, 1986

[54] ANIMAL LITTER

[75] Inventor: George R. Goss, Quincy, Ill.

[73] Assignee: Oil-Dri Corporation of America, Chicago, Ill.

[21] Appl. No.: 732,169

[22] Filed: May 8, 1985

[51] Int. Cl.[4] ............................................. A01K 1/015
[52] U.S. Cl. ...................................................... 119/1
[58] Field of Search ............................................. 119/1

[56] References Cited

U.S. PATENT DOCUMENTS 3,059,615 10/1962 Kuceski et al. ........................... 119/1
4,007,708 2/1977 Yacono .................................... 119/1
4,085,704 4/1978 Frazier .................................... 119/1
4,459,368 7/1984 Jaffee et al. ........................... 119/1 X
4,506,628 3/1985 Stockel ................................... 119/1
4,517,919 5/1985 Benjamin et al. ....................... 119/1

Primary Examiner—Robert P. Swiatek
Attorney, Agent, or Firm—Dressler, Goldsmith, Shore, Sutker & Milnamow, Ltd.

[57] ABSTRACT

Animal litter composition which includes a particulate, absorbent inorganic solid material and an odor-abating amount of p-hydroxybenzoate (paraben) distributed on the solid material is disclosed.

9 Claims, No Drawings

ANIMAL LITTER

TECHNICAL FIELD

This invention relates to animal litter compositions and to methods for manufacturing such compositions.

BACKGROUND ART

Particulate clay is by far the most common animal litter utilized by pet owners in litter boxes that are kept indoors. However, the development of odors in the litter boxes as they are utilized by a pet represents a serious problem.

Heretofore numerous attempts have been made to improve the deodorizing properties of animal litter. Illustrative of such attempts are U.S. Pat. Nos. 2,895,873 and 3,029,783 in which is disclosed the in-situ formation of aluminum sulfate by the reaction of sulfuric acid with the alumino silicates present in the clay together with the use of an onium compound as a germicide. U.S. Pat. No. 4,494,482 discloses solid absorbent materials having adsorbed thereon a halogenated aromatic hydrocarbon bacteriostat. U.S. Pat. No. 4,341,180 describes the use of bactericides such as cetylperidium chloride, cetalkonium chloride, and the like in pelletized rejects of a secondary fiber plant. The use of a disinfectant, germicide, or fungicide in poultry or animal bedding is also mentioned in U.S. Pat. No. 2,708,418.

Other attempts to resolve the odor problem include the controlled release of a masking fragrance when a clay litter material is wet by voided body fluids as described in U.S. Pat. Nos. 3,675,625, 3,921,581, 4,009,684 and 4,020,156 as well as the use of specific deodorizing materials such as chlorophyll, alkali metal dihydrogen phosphates, potassium acid phthalate, or combinations thereof, as described in U.S. Pat. No. 3,735,734. The use of ferrous sulfate heptahydrate for deodorizing animal litter is described in U.S. Pat. No. 3,776,188. An animal litter said to absorb and neutralize odors and prepared from a mixture of alfalfa, bentonite and a binder therefor is described in U.S. Pat. No. 3,789,787. A deodorant for animal litter consisting of magnesium carbonate and borax is described in U.S. Pat. No. 3,352,792. The use of Vitamin E in animal litter for odor-abatement is described in U.S. Pat. No. 4,007,708.

Materials and compositions other than clays but said to have odor abating properties have also been proposed as animal litter. Acid buffered cellulosic materials are described in U.S. Pat. No. 3,059,615. Dehydrated alfalfa is described in U.S. Pat. No. 3,286,691. A mixture of alfalfa with perlite or vermiculite is described in U.S. Pat. No. 3,425,397. Camphane derivatives in combination with organic or inorganic animal litters are described in U.S. Pat. No. 3,636,927.

Foamed plastics combined with deodorizers are described in U.S. Pat. No. 3,765,371. Cherry pit extract in combination with animal litter is described in U.S. Pat. No. 3,816,577. Animal litter derived from popcorn, alone or admixed with clay or alfalfa is described in U.S. Pat. No. 3,916,831. The use of peanut hulls containing sodium bicarbonate as animal litter is described in U.S. Pat. No. 3,983,842. The use of absorbent fly ash, bottom ash, boiler slag, with or without Fuller's earth and with or without an in-situ polymerized monomer having an acidic functional group is described in U.S. Pat. Nos. 4,129,094 and 4,506,628.

The foregoing diverse approaches to odor control in animal litter amply demonstrate that a practical solution to this problem has been elusive. Some of the heretofore proposed approaches have not proved to be commercially practical from a functional standpoint, from a toxicity standpoint, and/or from a cost standpoint.

It has now been found, however, that effective odor abatement can be achieved in animal litter derived from naturally-occurring as well as synthetic materials by means of an odor-abatement agent that is safe to the pet, relatively non-toxic, and relatively inexpensive.

SUMMARY OF THE INVENTION

The present invention contemplates an animal litter composition that contains an effective amount of a benzoic acid ester derived by esterifying benzoic acid with a $C_1$ to $C_4$ aliphatic alcohol. Specifically, the present composition comprises a particulate, absorbent, inorganic solid material having distributed thereon an odor-abating amount of a p-hydroxybenzoate represented by the formula

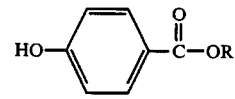

wherein R can be $C_1$ to $C_4$ alkyl, e.g., methyl, ethyl, propyl, isopropyl, butyl, isobutyl and tertiary butyl. The absorbent solid material may also carry a fragrance and/or Vitamin E.

While some of these p-hydroxybenzoates, also sometimes referred to as parabens, have been used heretofore as preservatives for food and cosmetic preparations because of their relatively low toxicity, they have also been criticized in the art as having insufficient bactericidal activity. Thus, the parabens would not be likely candidates for use as bactericides under much more challenging conditions such as those encountered with excrement in animal litter boxes. However, it has now been found that the lower alkyl esters of p-hydroxybenzoic acid, especially the propyl ester of p-hydroxybenzoic acid, perform well as odor-abatement agents in inorganic animal litter compositions. It is believed that the metal cations that are present in such inorganic compositions, e.g., zinc cations, magnesium cations, and the like, may exert a potentiating effect on the p-hydroxybenzoates. Also, the combined buffering capability of the clay-type animal litter compositions and the p-hydroxybenzoates is believed to enhance further the odor-abating performance of the present preferred compositions.

DESCRIPTION OF PREFERRED EMBODIMENTS

The solid particulate absorbent material suitable for present purposes can be a comminuted clay, and the like. The so-called Fuller's earth clay is a particularly well suited absorbent material and can be utilized alone or in combination with synthetic absorbent materials such as absorbent calcium sulfate dihydrate granules. The latter synthetic absorbent materials can also be utilized as the sole solid particulate absorbent material.

The Fuller's earth clay, also referred to herein as Fuller's earth or clay, constituent of the compositions of this invention is a natural, earthy material composed primarily of hydrous aluminum silicates, while small amounts of non-clay materials can also be present. Typical clays useful herein are montmorillonite, kaolin, illite, halloysite, hormite, vermiculite, the sodium and calcium bentonites (clays largely composed of montmorillonite but which can also contain beidellite, attapulgite, and similar minerals), attapulgite, sepiolite, and the like. Calcium bentonite and hormite are particularly preferred clays for the present purposes.

Calcium bentonites can range in color from a cream, off-white to a dark reddish tan color and are frequently referred to in the trade under designations such as Mississippi Brown and Mississippi White. Typical hormites are Georgia Brown and Georgia White. While the chemical and physical properties of the calcium bentonites differ to some extent from each other, from the hormites, and from other Fuller's earth clays, these properties are shared sufficiently that one of the clays can be used as exemplary of the whole class of Fuller's earth clays generally. Thus, the hormite clays Georgia White (GW) and Georgia Brown (GB) will generally be used herein and in the Examples as exemplary of the Fuller's earth clays.

Useful Fuller's earth clays typically have bulk densities of about 0.4 to about 0.9 kg/l, and more preferably have bulk densities of about 0.4 to about 0.65 kg/l.

Water and oil sorption, usually expressed as a percent of water and oil sorbed based on the weight of the clay particle, also act to define the clays. Useful Fuller's earth clays sorb water or oil in an amount of more than about 50 percent of the weight of the particle. More preferably, the clays sorb an amount of more than about 60 percent of their own weight, and most preferably sorb an amount of more than about 80 percent of their weight in water or oil. The maximum amount of water or oil sorption for Fuller's earth clays is believed to be about 120 percent of the weight of the clay particles.

Synthetic calcium sulfate dihydrate-containing granules useful for the purposes of this invention can be prepared by a number of methods, including the methods disclosed in U.S. Pat. Nos. 4,163,674 to Been; 4,183,763 to Omilinsky et al.; and 4,264,543 to Valenta; the disclosure of each of said patents is incorporated herein by reference to the extent pertinent. The synthetic calcium sulfate dihydrate granules suitable as the particulate absorbents can also include light weight naturally absorptive materials as is disclosed in the aforementioned U.S. Pat. No. 4,163,674; plaster-derived synthetic sorbent materials that include other inorganic substances such as calcium carbonate, portland cement, vermiculite, pumice, activated carbon, diatomaceous earth are also suitable.

The synthetic calcium sulfate dihydrate-containing granules typically contain at least about 50 weight percent calcium sulfate dihydrate and preferably have a bulk density of about 0.5 to about 0.9 kg/l, and more preferably of about 0.5 to about 0.8 kg/l. These granules preferably sorb oil or water in an amount of more than about 30 percent of their own weight, and more preferably in an amount of more than 50 percent of the weight of the granules. The particle size distribution of these granules is preferably such that no more than about 25 weight percent are passed through a 2 mesh sieve screen and are retained on a 6 mesh sieve screen. More preferably no more than about 15 weight percent are of a 2/6 size. All sieve sizes referred to herein are of the U.S. Standard Sieve Series.

Also suitable are mixtures of synthetic and clay sorbents of the type described in U.S. Pat. No. 4,459,368 to Jaffee et al. Typically in the latter mixtures the clay particles are present at about 5 to about 40 weight percent of the composition, while the synthetic granules are preferably present at about 95 to about 60 weight percent. More preferably, the clay particles comprise about 10 to about 30 weight percent of the composition and the synthetic granules comprise about 90 to about 70 weight percent. Most preferably, about 15 to about 25 percent of the weight of the composition is comprised of Fuller's earth clay particles while about 85 to about 75 percent by weight of the composition is comprised of synthetic calcium sulfate dihydrate granules.

The foregoing absorbent mixtures can also be utilized in systems wherein the clay and the synthetic granules do not constitute substantially all of the weight of the particular system, as where sorbent wood chips or sawdust are also present. In such instances the clay particles are preferably present relative to the synthetic particles in a ratio by weight of 0.5:9.5 to about 4:6. More preferably the weight ratio is about 1:9 to about 3:7. Most preferably, the weight ratio of clay particles to synthetic particles is about 1.5:8.5 to about 2.5 to about 7.5.

The odor-abating agents distributed on the solid but particulate absorbent material are p-hydroxybenzoates, i.e., the esters of p-hydroxybenzoic acid. These odor-abating agents can be represented by the formula

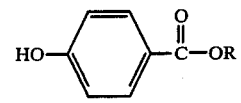

wherein R can be an alkyl group containing 1 to 4 carbon atoms, i.e., methyl, ethyl, propyl, isopropyl, butyl, isobutyl and tertiary butyl.

The odor-abating agent is present on the absorbent material in an odor-abating amount, preferably in an amount of about 0.01 to about 0.5 percent by weight of the absorbent material and more preferably in an amount of about 0.075 to about 0.125 percent by weight of the absorbent material.

The $C_1$ to $C_4$ alkyl esters of p-hydroxybenzoic acid are illustrated by methyl p-hydroxybenzoate, ethyl p-hydroxybenzoate, n-propyl p-hydroxybenzoate, isopropyl p-hydroxybenzoate, n-butyl p-hydroxybenzoate, isobutyl p-hydroxybenzoate, and mixtures of the foregoing.

Typically these particular agents are distributed on the solid, particulate absorbent material in an amount of about 0.1 percent by weight, based on the weight of the particulate absorbent material.

The aforementioned parabens are solids at room temperature and are relatively sparsely soluble in water. While these odor-abatement agents can be distributed on the particulate absorbent material by comingling a finely-divided paraben with the particulate absorbent material in a conventional blender, such as a ribbon blender, the parabens can also be first dissolved, if desired, in an aqueous monohydric or polyhydric alcohol solution, e.g., an aqueous ethanol or an aqueous propylene glycol solution, or the like. The solution is then sprayed onto the absorbent material while the latter is agitated so as to provide a substantially uniform distribution of the odor abatement agent on the solid absorbent material at the desired loading level of the former.

In addition to the foregoing essential odor-abatement constituent, the present animal litter compositions may also contain a natural or synthetic fragrance such as pine, humus, earth, or lemon fragrance, and the like, or a floral fragrance, e.g., rose, lilac, gardenia, orchid essence. The fragrance can be introduced onto the solid absorbent material as a water-soluble perfume. A wide variety of such perfumes and essence oils is commercially available.

In lieu of a fragrance, or in further addition thereto, the present animal litter compositions may also contain Vitamin E as an additional odor control agent. For distribution onto the solid absorbent material Vitamin E usually is dissolved in an oil such as a vegetable oil, e.g., corn oil, cottonseed oil, peanut oil, soybean oil, etc., or a mineral oil, e.g., paraffin oil. Vitamin E may be present in an amount of about 0.25 to about 5 percent by weight of the absorbent material. The resulting oil solution is then sprayed onto the particulate absorbent material while the latter is agitated.

This invention is further illustrated by the following examples.

EXAMPLE 1

Preparation of Clay-Based Animal Litter Composition

Particulate clay (Georgia White; 6×20 Mesh particle size) was admixed with propyl paraben powder. The amount of propyl paraben in the admixture was about 0.1 percent by weight of the clay present. The admixture was agitated by shaking until substantially uniform distribution of propyl paraben on the clay particles was obtained. Thereafter aliquots of the clay particles bearing propyl paraben were evaluated as animal litter.

EXAMPLE 2

Preparation of Clay-Based Animal Litter Composition

In a manner similar to Example 1, above, the particulate clay was admixed with benzoic acid and with p-hydroxybenzoic acid, respectively, in amounts providing a loading of about 0.076 percent by weight based on the weight of the clay present. The obtained product was then evaluated as animal litter.

EXAMPLE 3

Preparation of Clay-Based Animal Litter Composition

In a manner similar to Example 1, above, particulate clay was admixed with methyl paraben powder in an amount providing a loading of about 0.1 percent by weight based on the weight of the clay present. The obtained product was then evaluated as animal litter.

EXAMPLE 4

Preparation of Gypsum-Based Animal Litter Composition

Absorbent gypsum particles were prepared by pelletizing plaster of Paris from several commercial sources (National Gypsum, Westroc, Orth and Wisbech) on a disc pelletizer and as taught in U.S. Pat. No. 4,264,543 to Valenta. The produced gypsum pellets were then crushed and classified as to size. Gypsum particles passing though a 4 Mesh sieve and retained on a 20 Mesh sieve were selected and admixed with propyl paraben in an amount providing a loading of about 0.1 percent by weight of the gypsum, and the admixture was agitated until a substantially uniform product was obtained. Aliquots of the obtained product were then evaluated as animal litter.

EXAMPLE 5

Preparation of Test Inoculum

Model synthetic cat urine constituted by an aqueous solution of urea and other water soluble salts normally present in cat urine, specific gravity 1.06, was inoculated with cat feces in an amount of about 10 grams of feces per liter of solution. The obtained test inoculum (TI) was then used in the evaluation of animal litter compositions.

EXAMPLE 6

Evaluation of Clay-Based Animal Litter

Three aliquots of each clay-based animal litter to be evaluated (about 200 grams each, prepared as described in Examples 1 and 2, above) were placed in plastic jars and combined with about 170 milliliters of the test inoculum prepared as described in Example 5, above. After addition of the inoculum, the resulting mass was shaken to distribute the inoculum. The jars were then capped loosely and incubated at room temperature.

The incubating jars were periodically checked for odor, rated, and the pH of the jar contents was measured. Odor in each jar was determined by sniffing the jar immediately after the cap was removed therefrom. The following odor values were assigned: 0—natural odor, 1—cat box odor, 2—ammonia odor. The pH measurements were made as follows. A 25-gram sample was removed from each jar and slurried with water. The pH value reading was taken of the slurry using a pH meter equipped with a silver-silver chloride combination electrode.

The odor value ratings and pH measurements were then averaged for each instance and are reported in Table I, below. These data show that an ester of p-hydroxybenzoic acid outperforms other preservatives such as p-hydroxybenzoic acid and benzoic acid.

TABLE I

| Evaluation of Clay-Based Animal Litter | | | | |
|---|---|---|---|---|
| Georgia White Clay | Odor Value[1] (pH) on Day of Test | | | |
| (GW) + Additive | 3 | 5 | 6 | 9 |
| GW + test inoculum (TI) | 1(7.5) | 1.5(8.2) | 2(8.6) | 2(8.7) |
| GW + TI + propyl paraben, 0.1 wt % | 0.7(7.6) | 1(7.9) | 1.2(8.2) | 1(8.1) |
| GW + TI + p-hydroxy-benzoic acid, 0.076 wt % | 0.7(7.4) | 1.2(8.3) | 2(8.6) | 2(8.8) |
| GW + TI + benzoic acid, 0.076 wt % | 0.8(7.5) | 1(8.3) | 1.7(8.4) | 2(8.8) |

[1] 0 —natural, 1 —cat box, 2 —ammonia.

EXAMPLE 7

Evaluation of Gypsum-Based Animal Litter

Three aliquots of each gypsum-based animal litter preparation as described in Example 4, above, were evaluated using the procedure described in Example 6, above, except that 100 milliliters of the test inoculum were added to each jar. The results are compiled in Table II, below. These data demonstrate the effectiveness of paraben as an odor-abating agent on a gypsum-based synthetic absorbent.

TABLE II

Evaluation of Gypsum-Based Animal Litter

| Absorbent Gypsum + TI + Additive | Odor Value[1] (pH) on Day of Test | | | | | | |
|---|---|---|---|---|---|---|---|
| | 1 | 2 | 3 | 4 | 5 | 6 | 7 |
| Westroc + TI + propyl paraben, 0.1 wt-% | 0.5(7.5) | 0.5(7.6) | 1(7.7) | 1(7.9) | 1(7.9) | 1(8.1) | 1(7.9) |
| Orth + TI + propyl paraben, 0.1 wt-% | 0.5(7.3) | 0.5(8.0) | 1(8.1) | 1(8.2) | 1(8.1) | 1.5(8.4) | 1(8.1) |
| Wisbech + TI + propyl paraben, 0.1 wt-% | 0.5(7.8) | 0.8(7.9) | 1(8.0) | 1(8.1) | 1(8.0) | 1(8.1) | 1(8.0) |
| Wisbech only + TI | 0.5(7.8) | 1.3(8.0) | 1.3(7.9) | 1.3(8.1) | 1.3(8.1) | 1.3(8.4) | 1.7(8.3) |

[1] 0 —natural, 1 —cat box, 2 —ammonia.

EXAMPLE 8

Evaluation of Clay-Based Animal Litter Containing Methyl Paraben or Propyl Paraben Three 200-gram aliquots of each clay-based animal litter to be evaluated, prepared as described in Examples 1 and 3, were tested as described in Example 6, above, except that each aliquot was inoculated with 200 milliliters of the test inoculum. The results are compiled in Table III, below. These data demonstrate the odor-abatement efficacy of methyl paraben and of propyl paraben.

TABLE III

Evaluation of Clay-Based Animal Litter Containing Methyl Paraben or Propyl Paraben

| Georgia White Clay (GW) + Additive | Odor Value[1] (pH) on Day of Test | | | | | | | |
|---|---|---|---|---|---|---|---|---|
| | 1 | 2 | 3 | 4 | 5 | 6 | 7 | 8 |
| GW clay only, no additive | 0(6.8) | 0(6.7) | 0(6.8) | 0(6.4) | 0(6.5) | 0(6.5) | 0(6.6) | 0(6.5) |
| GW + TI, no paraben | 0.5(7.1) | 0.5(7.2) | 1(7.5) | 1(8.0) | 1.5(8.0) | 2(8.1) | 2(8.1) | 2(8.5) |
| GW + TI + methyl paraben, 0.1 wt % | 0.5(7.0) | 0.5(7.0) | 1(7.0) | 1(7.3) | 1(7.5) | 1(7.6) | 1.5(8.0) | 2(8.6) |
| GW + TI + propyl paraben, 0.1 wt % | 0.5(7.1) | 0.5(7.1) | 0.5(7.3) | 1(7.6) | 1(7.6) | 1.5(8.1) | 1.8(8.1) | 2(8.6) |

[1] 0 —natural, 1 —cat box, 2 —ammonia.

I claim:

1. An animal litter composition which comprises particulate, absorbent inorganic solid material which is a member of the group consisting of clay and gypsum and, distributed on said solid material, an odor-abating amount of a compound represented by the formula

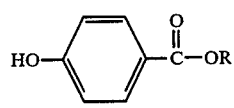

wherein R is a member of the group consisting of alkyl containing 1 to 4 carbon atoms.

2. The animal litter composition in accordance with claim 1 wherein the compound is methyl ester of p-hydroxybenzoic acid.

3. The animal litter composition in accordance with claim 1 wherein the compound is ethyl ester of p-hydroxybenzoic acid.

4. The animal litter composition in accordance with claim 1 wherein the compound is n-propyl ester of p-hydroxybenzoic acid.

5. The animal litter composition in accordance with claim 1 wherein the compound is isopropyl ester of p-hydroxybenzoic acid.

6. The animal litter composition in accordance with claim 1 wherein the compound is n-butyl ester of p-hydroxybenzoic acid.

7. The animal litter composition in accordance with claim 1 wherein the compound is isobutyl ester of p-hydroxybenzoic acid.

8. The animal litter composition in accordance with claim 1 and additionally containing a fragrance.

9. The animal litter composition in accordance with claim 1 and additionally containing Vitamin E.